(12) United States Patent
Qi et al.

(10) Patent No.: US 11,801,265 B2
(45) Date of Patent: Oct. 31, 2023

(54) PREPARATION METHOD OF NK CELLS AND USE THEREOF IN THE TREATMENT OF CANCER

(71) Applicant: SINO UNITED (BEIJING) BIOMEDICAL TECHNOLOGY CO., LTD., Beijing (CN)

(72) Inventors: Aijie Qi, Beijing (CN); Shaobo Li, Beijing (CN); Ailei Qi, Beijing (CN)

(73) Assignee: SINO UNITED (BEIJING) BIOMEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 17/582,097

(22) Filed: Jan. 24, 2022

(65) Prior Publication Data
US 2022/0233591 A1 Jul. 28, 2022

(30) Foreign Application Priority Data

Jan. 25, 2021 (CN) .......................... 202110092682.3

(51) Int. Cl.
| | | |
|---|---|---|
| *A61K 35/17* | (2015.01) | |
| *A61P 35/00* | (2006.01) | |
| *A61K 39/395* | (2006.01) | |
| *C12N 5/0783* | (2010.01) | |

(52) U.S. Cl.
CPC ........ *A61K 35/17* (2013.01); *A61K 39/39558* (2013.01); *A61P 35/00* (2018.01); *C12N 5/0646* (2013.01); *C12N 2500/02* (2013.01); *C12N 2501/2302* (2013.01); *C12N 2501/2315* (2013.01); *C12N 2501/2321* (2013.01)

(58) Field of Classification Search
CPC .............. A61K 35/17; A61K 39/39558; A61K 2039/505; A61K 39/39541; A61P 35/00; C12N 5/0646; C12N 2500/02; C12N 2501/2302; C12N 2501/2315; C12N 2501/2321; C12N 2506/115; C07K 2317/34; C07K 2317/73; C07K 2317/92; C07K 16/2896; C07K 2317/24; C07K 2317/56

See application file for complete search history.

(56) References Cited

U.S. PATENT DOCUMENTS

| | | | | |
|---|---|---|---|---|
| 2008/0089862 | A1* | 4/2008 | Benhar | ...................... A61P 1/16 435/23 |
| 2014/0023626 | A1* | 1/2014 | Peled | ...................... C12N 15/85 435/375 |
| 2021/0380678 | A1* | 12/2021 | Zhang | ................ C07K 16/2851 |

FOREIGN PATENT DOCUMENTS

| | | |
|---|---|---|
| CN | 107446888 A | 12/2017 |
| CN | 107460167 A | 12/2017 |

OTHER PUBLICATIONS

R&D Systems et al. Unit Conversion Table (https://www.rndsystems.com/resources/technical-information/unit-conversion-table) (Year: 2023).*
Wagner J et al. A Two-Phase Expansion Protocol Combining Interleukin (IL)-15 and IL-21 Improves Natural Killer Cell Proliferation and Cytotoxicity against Rhabdomyosarcoma. Front Immunol 2017 8:676 1-16 (Year: 2017).*
Lonza et al. TheraPEAK X-VIVO Hematopoietic Cell Culture Medium https://bioscience.lonza.com/lonza_bs/US/en/x-vivo-serum-free-media Oct. 2019 (Year: 2019).*

* cited by examiner

*Primary Examiner* — Julie Wu
*Assistant Examiner* — John J Skoko, III
(74) *Attorney, Agent, or Firm* — HAUPTMAN HAM, LLP

(57) ABSTRACT

The present disclosure relates to a method for preparing NK cells and an application thereof in treatment of a cancer. The present disclosure provides a pharmaceutical composition prepared from NK cells and a monoclonal antibody of CD105, which can be used for the treatment of colorectal cancer and has a good application prospect.

4 Claims, 2 Drawing Sheets

Specification includes a Sequence Listing.

PREPARATION METHOD OF NK CELLS AND USE THEREOF IN THE TREATMENT OF CANCER

RELATED APPLICATIONS

The present application claims priority from Chinese Application Number 202110092682.3, filed Jan. 25, 2021, the disclosure of which is hereby incorporated by reference herein in its entirety.

INCORPORATION BY REFERENCE

The sequence listing provided in the file entitled Sequence_Listing_Mod1.txt, which is an ASCII text file that was created on Mar. 15, 2022, and which comprises 2,386 bytes, is hereby incorporated by reference in its entirety.

TECHNICAL FIELD

The present disclosure relates to the field of pharmacy, and in particular, to a method for preparing NK cells and an application thereof in the treatment of a cancer.

BACKGROUND ART

NK cells are lymphoid cells having a variety of immunological functions. Human NK cells are CD56 and CD16 positive, and CD3 and CD19 negative. A small fraction of NK cells may be CD8 positive. The killing of tumor cells by NK cells is not restricted by MHC, nor does it require prior contact with antigens or any memory response. The advantages of NK cells in killing tumors are manifested in two aspects: direct lysis and secretion of cytokines. NK cells can kill tumors through either perforin or Fas ligand. NK cells can produce TNF-a, IFN-γ, and IL-1, which play an important role in the anti-cancer effect of NK cells. NK cells have the ability to rapidly reject allogeneic bone marrow, but do not mediate the transplant rejection of solid tissue.

During the occurrence and development of tumors, NK cells can be activated either by directly recognizing malignantly transformed cancer cells through "internal recognition" (such as NCRs, NKG2D, SLAMs, DNAMs, etc.), or by helper cells such as monocytes, macrophages, or dendritic cells, etc. These helper cells respond to changes in an internal or external environment through their pattern recognition receptors (including cell surface receptors TLR2, TLR4, intracellular cytoplasmic receptors RIG-1, NALP3, NOD2, endosomal receptors TLR7, TLR9, etc. that recognize a variety of pathogens), and then transmit signals to NK cells by secreting a variety of soluble factors or by direct contact, so that NK cells may exert their killing function and secrete inflammatory cytokines. In humans, the soluble factors that have been confirmed include IL-12, IL-18, IFN, IL-2, and TNF; and the molecules in direct contact include GITRL/GITR, IL-12/IL-12R, CD48/2B4, MICAorMICBo-rULBP1-ULBP3 /NKG2D, AICL/NKp80, IL-15R-IL-15/IL-15βγ, and the like.

In the treatment of tumors by using NK cells, not only stimulating factors (such as IL-2, IL-12, IL-15, etc.) may be used, but also blockers against KIR on NK cells may be used. In addition, it is also suggested that blocking the function of KIR on NK cells may improve the anti-cancer immune response of the organism, just as by blocking the negative signal of CTLA4 to T cells. The above data suggest that activated NK cells may not only directly undergo adoptive infusion to treat tumors, but also block the KIR of these NK cells to enhance their anticancer effects.

Recently, there have been reported several approaches that can enhance the in vitro expansion of NK cells, their persistence in vivo, and their homing to the tumor microenvironment, thereby increasing their antitumor effects. In early time, NK cell expansion methods used media containing only cytokines, such as IL-2 and IL-15, for only 10-20-fold expansion. Subsequently, by using feeder cells in combination with cytokines, the cells may expand by up to 80~10,000-fold, especially with CD3-depleted PBMCs. More recently, by using CD3-depleted apheresis products, NK cells with >95% purity may be obtained by using feeder-free MEM-a medium containing IL-2, IL-15, and vitamin B3. IL-15 promotes NK cell growth and proliferation without activating Treg cells. Heterodimeric IL-15 (IL-15-sIL-15Rα) may more effectively stimulate NK cell proliferation. NK cells express IL-12Rβ2, and high doses of IL-12 have immunomodulatory effects on NK cells and can promote the production of IFN-γ. Lenalidomide, an immunomodulatory agent, may indirectly increase the proliferation and cytotoxicity of NK cells through IL-2 and IFN-γ. PD1- and PDL1-specific monoclonal antibodies in combination with Lenalidomide may improve the ability of NK cells to fight myeloma. PD1 blockers may enhance NK cell-induced ADCC and migration of NK cells to tumors, while inhibiting functions of Treg cells. TRAIL, the death ligand of NK cells, may induce apoptosis of TRAILR-positive tumor cells, and histone acetylase and proteasome inhibitors may enhance the function of this pathway. In a phase I clinical trial, bortezomib combined with autologous NK cells resulted in tumor regression in refractory renal cell carcinoma and chronic leukemia.

Colorectal cancer is one of the most common malignant tumors of the digestive system. Statistics showed that the incidence rate of this cancer ranks third among malignant tumors throughout the world, and has risen to second in western countries and economically developed regions in China. Colorectal cancer is also one of the leading causes of cancer-related death worldwide. Although bevacizumab has been widely used in the treatment of carcinoma of the large intestine, the toxic and side effects of bevacizumab, including bleeding and thrombotic events, have also attracted attention. Therefore, the development of a new monoclonal antibody capable of treating carcinoma of the large intestine (colorectal cancer) still has great application value. In particular, the use of NK cells in combination with monoclonal antibodies is the current focus of combined therapy.

SUMMARY OF THE INVENTION

The present disclosure overcomes the defects of the prior art and provides a new method for effectively treating carcinoma of the large intestine, particularly colorectal cancer.

In one aspect of the present disclosure, an isolated NK cell is provided for the treatment of carcinoma of the large intestine, particularly colorectal cancer.

In another aspect, the present disclosure also provides a monoclonal antibody specific for CD105. Specifically, the monoclonal antibody of CD105 provided herein comprises a light chain variable region having an amino acid sequence of SEQ ID NO:1, and a heavy chain variable region having an amino acid sequence of SEQ ID NO:2.

In another aspect, there is also provided a pharmaceutical composition comprising the monoclonal antibody of CD105 provided herein and a pharmaceutically acceptable carrier.

In another aspect, there is also provided a pharmaceutical composition comprising the NK cells provided herein and a pharmaceutically acceptable carrier.

In another aspect, there is also provided a pharmaceutical composition comprising the NK cells provided herein, the monoclonal antibody of CD105 provided herein, and a pharmaceutically acceptable carrier.

In still another aspect, there is provided use of NK cells in preparing a medicament for treating colorectal cancer.

In yet still another aspect, there is provided use of the monoclonal antibody of CD105 in preparing a medicament for treating colorectal cancer.

In still another aspect, there is provided use of NK cells and the monoclonal antibody of CD105 in preparing a medicament for treating colorectal cancer.

Furthermore, the antibody provided herein is a full-length antibody, which is a conventional antibody full-length protein in the art, having heavy chain variable regions, light chain variable regions, heavy chain constant regions, and light chain constant regions. The heavy chain variable regions and light chain variable regions of the protein, together with human heavy chain constant regions and human light chain constant regions, constitute a fully human antibody full-length protein. Preferably, the full-length protein of the antibody is IgG1, IgG2, IgG3, or IgG4.

The present disclosure also provides a nucleic acid encoding the foregoing antibody.

The reagents and raw materials used herein are all commercially available.

The positive improvement effect of the present disclosure lies in that: the present disclosure provides a pharmaceutical composition prepared from NK cells and the monoclonal antibody of CD105, which can be used for the treatment of colorectal cancer. It has good application prospects.

DETAILED DESCRIPTION OF THE INVENTION

Figure 1:
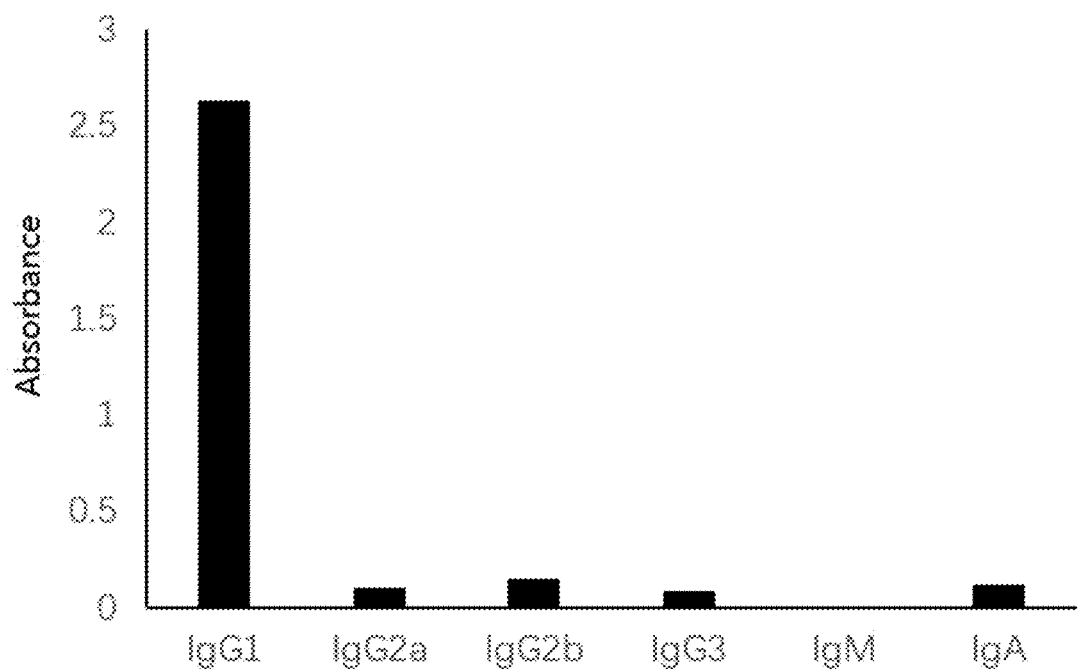
FIG. 1 shows the antibody subtype identification results.

The present disclosure is further described below by way of examples, but is not limited to the scope of the described examples. The experimental methods that do not specify specific conditions in the following examples are selected according to conventional methods and conditions, or according to the product description.

EXAMPLE 1

Preparation of NK Cells

Umbilical cord blood mononuclear cells were isolated by Ficoll-Hypaque density gradient centrifugation method, washed with PBS three times, and suspended in EX vivo-15 serum-free culture medium. The mononuclear cell concentration was adjusted to $3 \times 10^6$ cells/ml. To a culture flask coated with anti-CD3 antibody, 5ml of cell suspension and cytokines IL-2 (1000u/ml), IL-15 (50ng/ml), and IL-21 (30ng/ml) were added. The culture flask was then placed in an incubator with 5% $CO_2$ at 37° C., and cultured for 18 days. During the period, depending on the color of the culture medium and the size of NK cell colonies, the culture medium was supplemented in half amount, and the cytokines were supplemented in full amount. For supplementing the cytokines for the first time, 1000 u/ml of IL-2, 50 ng/ml of IL-15, and 30 ng/ml of IL-21 were added. From the second time, 1000 u/ml of the cytokine IL-2 and 50 ng/ml ml of IL-15 were added. After 18 days, cell phenotypes before and after cell expansion were detected by flow cytometry, and the CD56+CD3-cells reached (81.53±2.53) %.

EXAMPLE 2

Preparation of Anti-CD105 Monoclonal Antibody

1. Preparation of Antigen

According to the amino acid sequence of human CD105, a highly immunogenic epitope peptide, also called antigenic peptide FVLRSAYSSCGMQVSASMISNEAVV-NILSSSSPQRK, was obtained by screening, and was synthesized by Sangon Biotech (Shanghai) Co., Ltd.

2. Preparation of Hybridoma Cells

BALB/c mice were immunized. First immunization: 100 μL, of CFA was added to 100 μL, of 0.5 mg/mL CD105 antigenic peptide for emulsification, and the obtained emulsion was used to immunize 8-week-old mice. Second immunization: 3 weeks after completion of the first immunization, 100 μL, of IFA was added to 100 μL, of 0.5 mg/mL CD105 antigenic peptide for emulsification, and the obtained emulsion was used to immunize the mice for the second time. Third immunization: Third immunization was performed 3 weeks after completion of the second immunization. The method was the same as that for the second immunization. On the 10th day after completion of the third immunization, tail vein blood was collected to measure the antibody titer. A 96-well ELISA plate was coated with 1 ug/mL CD105 antigenic peptide solution. 1:100 mouse serum was diluted at multiple times in the 96-well ELISA plate to measure the antibody titer in mouse serum. Three mice with an antibody titer of over 1:10000 were selected for cell fusion. The spleens were taken from the three immunized mice, and placed into a sterile tissue culture dish with 4 mL of cell culture medium (containing 2% RPMI1640, 0.2% $NaHCO_3$, 1% Penicillin-streptomycin, and 10% inactivated fetal bovine serum), and smashed. NS-1 myeloma cells and mouse spleen cells were mixed in a 50mL centrifuge tube at a ratio of 1:10, and centrifuged at 1500 r/min for 5 min. After removal of the supernatant, 1mL 50% PEG3000 was slowly added. After washing the PEG3000 off with RPMI1640 medium, hybridoma cells were screened by cloning method in hemiglial medium, which comprises: culturing hybridoma cells in a 96-well cell culture plate (37° C., 5% CO2); and 3 days later, using indirect ELISA method to screen the positive grown cell clone wells, with an antibody positive rate of hybridoma cells being 9.53%. The four most significantly positive monoclonal hybridoma cells were cloned and subcloned by limiting dilution method.

Finally, two hybridoma cell lines which can secret anti-CD105 monoclonal antibody were obtained, named 1A4 and 4C6 respectively.

Mice were immunized with the two hybridoma cell lines, respectively, to collect ascites fluid. The monoclonal antibodies in the ascites fluid were routinely purified by using protein A column, followed by protein concentrating for use. As determined by Lowry method, the antibody 1A4 had a concentration of 2.1 mg/mL and the 4C6 had a concentration of 2.3 mg/mL.

EXAMPLE 3

Subtype identification and titer evaluation of the monoclonal antibody 1A4 The mouse monoclonal antibody typing kit was used for identification the subtype, and the operation steps were carried out in strict accordance with the instructions. The results were shown in FIG. 1.

The monoclonal antibody 1A4 was identified as immunoglobulin G1 class (FIG. 1).

Determination of titer of the monoclonal antibody: the concentrated antibody was serially diluted at 1: 1000, 1: 2000, 1: 4000, 1: 8000, 1: 16 000, 1: 32 000, 1: 64 000, 1: 128 000, 1: 256 000, and 1: 512 000, and then the dilutions were added to the microtiter plate coated with the antigenic peptide, to measure the A450 nm values by indirect ELISA method, which were then plotted versus the dilution degree values. The dilution degree value when A450 nm was 0.1 was defined as its titer. As a result, the titer of the monoclonal antibody 1A4 was about 1:512000.

EXAMPLE 4

Affinity identification and sequence identification of the monoclonal antibody 1A4

The binding ability of the monoclonal antibody 1A4 to the antigenic peptide was identified by SPR method. Specifically, the binding kinetics of the monoclonal antibody 1A4 to the antigenic peptide was measured by the surface plasmon resonance (SRP) method with the BIAcoreX100 instrument, the antigenic peptide was directly coated on the CM5 biosensor chip. For kinetic measurements, the monoclonal antibody 1A4 was serially diluted three-fold with HBS-EP+ 1X buffer, injected at 25° C. for 120 s, dissociated for 30 min, and regenerated by adding 10 mM glycine-HCl (pH 2.0) for 120 s. The equilibrium dissociation constant (kD) of the monoclonal antibody 1A4 and the antigenic peptide was calculated using a simple one-to-one Languir binding model. The calculation results were shown in Table 1.

TABLE 1

Dissociation constants of the monoclonal antibody

| Monoclonal antibodies | Equilibrium dissociation constant |
|---|---|
| the monoclonal antibody 1A4 | 2.43E-11 |

It can be seen from Table 1 that the dissociation constant of the monoclonal antibody 1A4 was 2.43E-11, which indicates that the monoclonal antibody 1A4 of the present disclosure has a better effect of binding antigenic peptides.

The sequences of the light chain variable region and heavy chain variable region of the monoclonal antibody were identified by PCR, as follows:

```
Light chain variable region
                                     (SEQ ID NO: 1)
DIVITQSPALAAASPGEKVTITCAVSGGISDIYLHWYQQKSGIS

PKPWIYSTSWIAGGVPARFSGSGSGTSYSLTITSMEAEDAATYY

CDDWSCIPLCFGAGTKLELK

Heavy chain variable region
                                     (SEQ ID NO: 2)
EVQLEESGTELRRPGASVKLSCKASGYIFSSYLMSWIKQRPGQG

LEWIGGIYVGSSDTRYTSGFAGKATLTADKSSTAYMQLSSLAS

EDSAVYYCAGSNMMEDCWGLGTTLAVSS
```

EXAMPLE 5

Experiment of the monoclonal antibody 1A4 inhibiting cells

Human colon cancer LOVO cells (Cat. No.: CL-0144, Wuhan Procell Life Science & Technology Co., Ltd.)

The cytotoxic effect of the monoclonal antibody 1A4 on LOVO cells was detected by MTT method. LOVO cells in the logarithmic growth phase were digested with 0.25% trypsin, and made into a single cell suspension, which was then added to a 96-well culture plate, with 100 μl per well, and at a final cell density of $3 \times 10'$ cells/ml. Several experimental groups and a control group were set up with four replicates in each group. The cells were cultured at 37° C., 5% CO2 for 24h. For the experimental groups, 200 μl of the monoclonal antibody solution with a final mass concentration of 0.1, 0.2, 0.3, 0.4, or 0.5 mg/ml was added respectively. For the control group, mouse IgG was added for 24 h of incubation. 20 μl of 0.5 mg/ml MTT solution was added to each well, and incubated in the dark for another 4 h. The supernatant was discarded, and 200 μl of DMSO was added to each well for shaking, and the absorbance at 490 nm was measured with a microplate reader. The measurement was repeated for three times. The cell inhibition rate (%) was calculated as follows: the inhibition rate =(the value for the control group—the value for the experimental group)/the value for the control group x 100%.

Figure 2:
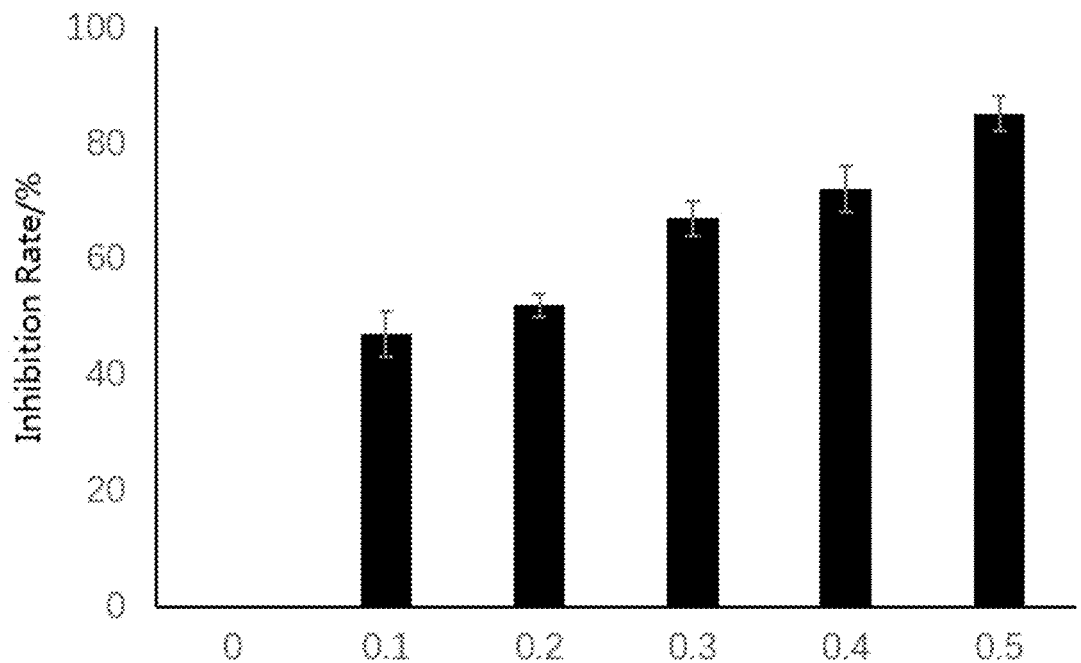
FIG. 2 shows the inhibitory effect of the monoclonal antibody on LOVO cells.

It can be seen from FIG. 2 that the monoclonal antibody 1A4 has an inhibitory effect on the growth of LOVO cells, and with the increasing of the antibody concentration, the inhibition rate of the growth of LOVO cells also increases, indicating a significant dose correlation, and the inhibition rate reached up to 85% at a concentration of 0.5 mg/ml.

EXAMPLE 6

Western blotting to detect the experimental groups for the effect on the expression of apoptotic proteins LOVO cells in the logarithmic growth phase were digested with 0.25% trypsin, and made into a single cell suspension, which was then added to a 6-well culture plate, at a final cell density of $3 \times 10^5$ cells/ml. The cells were cultured at 37° C., 5% $CO_2$ for 24 h. The culture medium was poured. For the experimental group 1, the monoclonal antibody was added at a final concentration of 0.5mg/ml; for the experimental group 2, the monoclonal antibody was added at a final concentration of 0.5mg/ml and concurrently NK cells were added at a final concentration of $3 \times 10^5$ cells/ml; and for the experimental group 3, NK cells were added at a final concentration of $3 \times 10^5$ cells/ml; and for the control group, DMEM medium was added, for 24 hours of treatment. The isolated LOVO cells were lysed with RAPI lysis buffer on ice to extract the total proteins, which were then separated by 12% SDS-PAGE. Specifically, the gel was placed in the membrane transfer buffer at 90 V for 45 min, during which the proteins were transferred onto the PVDF membrane. To the PVDF membrane, the primary antibody was added and incubated for 1 h, followed by washing 3 times with the washing buffer. Then the secondary antibody labeled with human HRP was added and incubated for 1 h, followed by washing and ECL color development. The expressions of caspase-3 and cleaved caspase-3 were detected by Western blotting. The results were shown as the relative expression level over the expression level of the control group, which were shown in Table 2.

TABLE 2

Results of the relative expression levels of apoptotic proteins

| Group | Relative expression level of caspase-3 | Relative expression level of cleaved caspase-3 |
| --- | --- | --- |
| Experimental group 1 | 0.71 ± 0.05 | 1.33 ± 0.11 |
| Experimental group 2 | 0.59 ± 0.03 | 1.63 ± 0.09 |
| Experimental group 3 | 0.83 ± 0.06 | 1.21 ± 0.07 |

As can be seen from the results in Table 2, for all the three experimental groups the signal of the cleaved caspase-3 was enhanced and the signal of caspase-3 was weakened, where the combination of the monoclonal antibody and NK cells can induce apoptosis of LOVO tumor cells most effectively, with the relative expression of the cleaved caspase-3 reaching 1.63±0.09.

EXAMPLE 7

In vivo anti-tumor experiment to observe the effect of NK cells and the monoclonal antibody of the present disclosure alone or in combination on the growth of LOVO cell transplanted tumor The LOVO cells in the logarithmic growth phase were digested and washed twice with PBS. The cell density was adjusted to $1\times10^7$ cells/ml, and 0.2 ml was subcutaneously inoculated into each BALB/nu male nude mouse. When the tumor mass grew to 100mm$^3$, nude mice were randomly divided into normal saline control group, NK combined with the monoclonal antibody group, NK group, and the monoclonal antibody treatment group, with 6 mice per group. Mice were injected intravenously with drugs, where 100 μl of NK cells at a concentration of $11\times10^7$/ml, and the monoclonal antibody at 5mg/kg were injected once every 4 days for a total of 4 weeks. The maximum longitudinal diameter (a) and the maximum transverse diameter (b) of the tumor in nude mice were measured with a vernier caliper every 4 days after starting the treatment, and the growth of the tumor was observed. The tumor volume =$0.5\times a\times b^2$. On the 28th day, the nude mice were sacrificed, to isolate and weigh the tumor tissue, and calculate the tumor inhibition rate. Tumor inhibition rate (%)=(1 -the average tumor mass for the experimental group/the average tumor mass for the control group) x100%.

Figure 3:
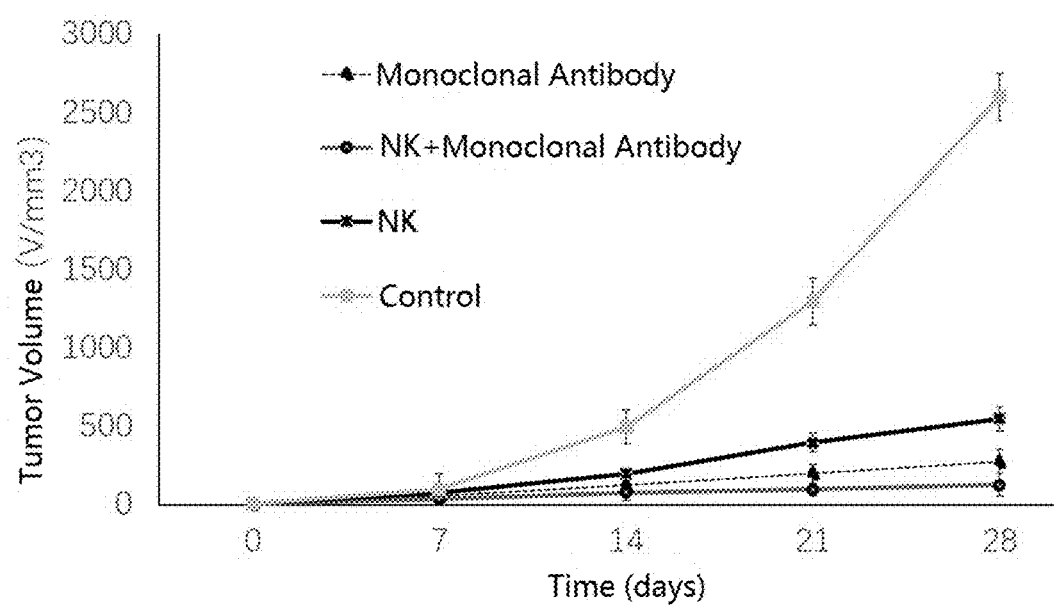
FIG. 3 shows the inhibitory effect of drugs on transplanted tumors.

It can be seen from FIG. 3 that the inhibitory effect of the NK cells combined with the monoclonal antibody administration group on the transplanted tumor was significantly stronger than the effect of the two single drugs (FIG. 3). The NK cells combined with the monoclonal antibody group had the most significant inhibition on the increasing of tumor weight, and the tumor's volume was only about 130 mm$^3$, indicating a good inhibitory effect.

The invention claimed is:

1. A pharmaceutical composition comprising:
   a monoclonal antibody of CD105 and
   a pharmaceutically acceptable carrier;
   wherein the monoclonal antibody of CD105 is a monoclonal antibody, which comprises a light chain variable region having an amino acid sequence of SEQ ID NO: 1, and a heavy chain variable region having an amino acid sequence of SEQ ID NO: 2.

2. A method for treating colorectal cancer in a subject in need thereof, comprising the step of administrating to the subject a therapeutically effective amount of the pharmaceutical composition according to claim 1.

3. The pharmaceutical composition according to claim 1, further comprising NK cells,
   wherein the NK cells are prepared by a procedure comprising:
      isolating umbilical cord blood mononuclear cells by using Ficoll-Hypaque density gradient centrifugation method;
      washing the isolated mononuclear cells three times with PBS;
      suspending the washed isolated mononuclear cells in a serum-free culture medium to form a cell suspension;
      adjusting the concentration of the mononuclear cells in the cell suspension to $3 \times 10^6$ cells/ml;
      adding 5 ml each of the cell suspension, cytokine IL-2 (1000 u/ml), cytokine IL-15 (50 ng/ml), and cytokine IL-21 (30 ng/ml) to a culture flask coated with an anti-CD3 antibody to form an initial culture composition;
      continuously culturing the culture composition under 5% $CO_2$ at 37° C. for 18 days;
      performing a first supplementation of the culture composition by adding the serum-free culture medium in half amount, 1000 u/ml of cytokine IL-2, 50 ng/ml of cytokine IL-15, and 30 ng/ml of cytokine IL-21; and
      performing a second supplementation of the culture composition by adding 1000 u/ml of the cytokine IL-2 and 50 ng/ml of cytokine IL-15.

4. A method for treating colorectal cancer in a subject in need thereof, comprising the step of administrating to the subject a therapeutically effective amount of the pharmaceutical composition according to claim 3.

* * * * *

SEQUENCE LISTING

```
<160> NUMBER OF SEQ ID NOS: 2

<210> SEQ ID NO 1
<211> LENGTH: 108
<212> TYPE: PRT
<213> ORGANISM: Artificial Sequence
<220> FEATURE:
<223> OTHER INFORMATION: Synthesized

<400> SEQUENCE: 1

Asp Ile Val Ile Thr Gln Ser Pro Ala Leu Ala Ala Ala Ser Pro Gly
1               5                   10                  15

Glu Lys Val Thr Ile Thr Cys Ala Val Ser Gly Gly Ile Ser Asp Ile
            20                  25                  30

Tyr Leu His Trp Tyr Gln Gln Lys Ser Gly Ile Ser Pro Lys Pro Trp
        35                  40                  45

Ile Tyr Ser Thr Ser Trp Ile Ala Gly Gly Val Pro Ala Arg Phe Ser
    50                  55                  60

Gly Ser Gly Ser Gly Thr Ser Tyr Ser Leu Thr Ile Thr Ser Met Glu
65                  70                  75                  80

Ala Glu Asp Ala Ala Thr Tyr Tyr Cys Asp Asp Trp Ser Cys Ile Pro
                85                  90                  95

Leu Cys Phe Gly Ala Gly Thr Lys Leu Glu Leu Lys
            100                 105

<210> SEQ ID NO 2
<211> LENGTH: 116
<212> TYPE: PRT
<213> ORGANISM: Artificial Sequence
<220> FEATURE:
<223> OTHER INFORMATION: Synthesized

<400> SEQUENCE: 2

Glu Val Gln Leu Glu Glu Ser Gly Thr Glu Leu Arg Arg Pro Gly Ala
1               5                   10                  15
```

```
Ser Val Lys Leu Ser Cys Lys Ala Ser Gly Tyr Ile Phe Ser Ser Tyr
            20              25                  30

Leu Met Ser Trp Ile Lys Gln Arg Pro Gly Gln Gly Leu Glu Trp Ile
        35              40                  45

Gly Gly Ile Tyr Val Gly Ser Ser Asp Thr Arg Tyr Thr Ser Gly Phe
    50                  55                  60

Ala Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Gly Ser Asn Met Met Glu Asp Cys Trp Gly Leu Gly Thr Thr Leu
            100                 105                 110

Ala Val Ser Ser
            115
```